(12) United States Patent
McLain

(10) Patent No.: US 8,449,582 B2
(45) Date of Patent: May 28, 2013

(54) CERVICAL FUSION APPARATUS AND METHOD FOR USE

(75) Inventor: Robert F. McLain, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1115 days.

(21) Appl. No.: 11/711,938

(22) Filed: Feb. 28, 2007

(65) Prior Publication Data
US 2007/0233118 A1 Oct. 4, 2007

Related U.S. Application Data

(60) Provisional application No. 60/778,534, filed on Mar. 2, 2006.

(51) Int. Cl.
A61B 17/88 (2006.01)

(52) U.S. Cl.
USPC .......................................................... 606/281

(58) Field of Classification Search
USPC .................................. 606/280–281, 286, 902
See application file for complete search history.

(56) References Cited

U.S. PATENT DOCUMENTS

| 5,364,399 | A | 11/1994 | Lowery et al. | |
| 5,549,612 | A | 8/1996 | Yapp et al. | |
| 5,616,144 | A | 4/1997 | Yapp et al. | |
| 5,690,629 | A | 11/1997 | Asher et al. | |
| 5,728,127 | A | 3/1998 | Asher et al. | |
| 5,741,255 | A | 4/1998 | Krag et al. | |
| 5,743,907 | A | 4/1998 | Asher et al. | |
| 5,800,433 | A | 9/1998 | Benzel et al. | |
| 2002/0045897 | A1* | 4/2002 | Dixon et al. | 606/61 |
| 2004/0034356 | A1 | 2/2004 | LeHuec et al. | |
| 2004/0097938 | A1* | 5/2004 | Alleyne | 606/69 |
| 2004/0177847 | A1 | 9/2004 | Foley et al. | |
| 2005/0085913 | A1 | 4/2005 | Fraser et al. | |
| 2005/0177161 | A1* | 8/2005 | Baynham et al. | 606/69 |
| 2006/0241615 | A1* | 10/2006 | Melkent | 606/69 |

* cited by examiner

Primary Examiner — Kevin T Truong
Assistant Examiner — Sameh Boles
(74) Attorney, Agent, or Firm — Tarolli, Sundheim, Covell & Tummino LLP

(57) ABSTRACT

In an exemplary embodiment of the present invention, a method of implanting a fusion plate, having at least two primary fastener openings, into a patient is described. According to the inventive method, a throat of the patient is dissected, providing access through the throat dissection to a spinal column of the patient. The fusion plate is inserted into the throat dissection, and the fusion plate is then positioned in an asymmetrical relationship with a sagittal plane of the spinal column. A first primary fastener is inserted through a first primary fastener opening of the fusion plate and into the first vertebra. A second primary fastener is inserted through a second primary fastener opening of the fusion plate and into the second vertebra. A cervical fusion apparatus is also disclosed.

8 Claims, 2 Drawing Sheets

CERVICAL FUSION APPARATUS AND METHOD FOR USE

RELATED APPLICATION

This application claims priority from U.S. Provisional Application No. 60/778,534, filed Mar. 2, 2006, the subject matter of which is incorporated herein by reference.

TECHNICAL FIELD

The present invention relates to an apparatus and method for use in retaining vertebrae of a spinal column in a desired spatial relationship. The present invention is particularly adapted for use in retaining cervical vertebrae of a human spinal column in a desired spatial relationship so that fusion of the cervical vertebrae can occur.

BACKGROUND OF THE INVENTION

The vertebrae of the human spinal column are commonly classified by position into cervical (neck), thoracic (chest), and lower back (lumbar) vertebrae, with intervertebral discs separating each vertebra from the adjacent vertebrae. In the neck, degeneration of discs often causes vertebrae to undesirably compress their associated spinal nerves, causing uncomfortable symptoms such as pain, numbness, weakness, and disordered reflex symptoms. Degenerated cervical discs may be treated by resection of the discs utilizing a surgical approach through the neck. Once the resection is completed, common procedure is to fuse the vertebrae adjoining the former position of the removed disc. Other conditions which may require fusion include treatment of fractured or broken vertebrae, correction of deformities, treatment of herniated discs, treatment of tumors, treatment of infections, or treatment of instability.

Fusion is a surgical technique in which one or more of the vertebrae of the spine are united or joined to prevent relative movement. The spinal fusion procedure does not directly connect the vertebrae; rather, a bone graft or spacer is positioned between endplates of adjacent vertebrae of the spine during surgery. Over a period of time healing occurs as living bone from vertebrae spans the intervertebral graft and connects the adjacent vertebrae together. Fusion is complete when living bone has completely spanned the graft and the adjacent vertebrae are thus connected by a solid bridge of bone.

Various apparatus are known for retaining vertebrae of a spinal column in a desired spatial relationship so that fusion of the vertebrae can occur. Such known apparatus can include rod or plate systems, with either commonly being attached to the vertebrae with bone screws, hooks, or other structures. For example, anterior fusion of the cervical spine is commonly stabilized using a fixation plate screwed to the vertebrae. The rods and/or plates can be temporary (removed after fusion of the vertebrae is complete) or permanent.

However, currently available plates are generally larger than needed to simply maintain adjacent cervical vertebrae in fixed orientation in most patients. These oversized structures require a relatively large incision and dissection for insertion, which may be complex and time-consuming for the surgeon and require broader dissection of tissues in the neck and greater pressure on tissues being moved out of the way. This generally results in longer healing time and a larger risk of complications in the patient than in a smaller incision and dissection.

Furthermore, the known plates are placed symmetrically with respect to a frontal midline of the spine, and the patient's trachea, larynx, and/or esophagus must be moved aside for access across that midline in the cervical region of the spine. Disturbance of these delicate throat structures often leads to hoarseness, pain, and swallowing difficulties.

SUMMARY OF THE INVENTION

In an exemplary embodiment of the present invention, a method of implanting a fusion plate, having at least two primary fastener openings, into a patient is described. According to the inventive method, a throat of the patient is dissected, providing access through the throat dissection to a spinal column of the patient. The fusion plate is inserted into the throat dissection, and the fusion plate is then positioned in an asymmetrical relationship with a sagittal plane of the spinal column. A side portion of an anterior surface of a first vertebra of the spinal column and a side portion of an anterior surface of a second vertebra of the spinal column are contacted by the fusion plate. A first primary fastener, having a longitudinal axis, is inserted through a first primary fastener opening of the fusion plate and into the first vertebra such that the longitudinal axis of the first primary fastener is angled within the sagittal plane relative to a transverse plane of the spinal column. A second primary fastener, having a longitudinal axis, is inserted through a second primary fastener opening of the fusion plate and into the second vertebra such that the longitudinal axis of the second primary fastener is angled within the sagittal plane relative to the transverse plane of the spinal column.

In an exemplary embodiment of the present invention, a method of retaining vertebrae of a spinal column in a desired spatial relationship is described. According to the inventive method a fusion apparatus including a fusion plate and at least two fasteners, each fastener having a longitudinal axis, is provided; the fusion plate is positioned in an asymmetrical relationship with a sagittal plane of the spinal column; and a first vertebra and a second vertebra are contacted by the fusion plate. A first primary fastener is inserted through a first primary fastener opening of the fusion plate and into the first vertebra such that the longitudinal axis of the first primary fastener is angled within the sagittal plane relative to a transverse plane of the spinal column. A second primary fastener is inserted through a second primary fastener opening of the fusion plate and into the second vertebra such that the longitudinal axis of the second primary fastener is angled within the sagittal plane relative to the transverse plane of the spinal column.

In an exemplary embodiment of the present invention, a cervical fusion apparatus is described. The cervical fusion apparatus includes a fusion plate and at least two primary fasteners. The fusion plate has at least two primary fastener openings and is adapted to simultaneously engage at least two vertebrae of a spinal column while being positioned asymmetrically about a sagittal plane of the spinal column. Each primary fastener has a longitudinal axis and is adapted for insertion through at least one primary fastener opening of the fusion plate. The longitudinal axes of the primary fasteners are each located within the sagittal plane and angled relative to a transverse plane of the spinal column when the primary fasteners are inserted through the primary fastener openings.

BRIEF DESCRIPTION OF THE DRAWINGS

For a better understanding of the invention, reference may be made to the accompanying drawings, in which.

DESCRIPTION OF EMBODIMENTS

Figure 1:
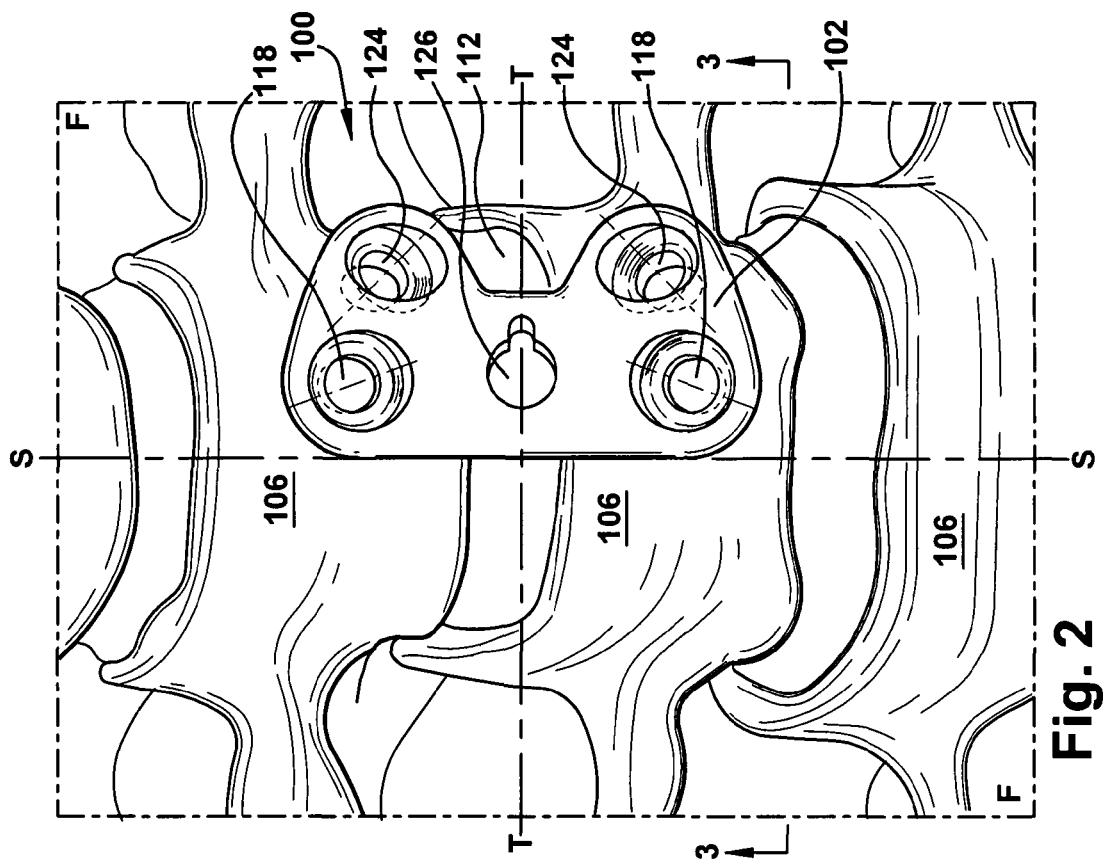
FIG. 1 is a frontal view of an exemplary embodiment of the present invention in a first mode.

In accordance with the present invention, FIG. 1 depicts a frontal view of a cervical fusion apparatus 100. The cervical fusion apparatus 100 includes a cervical fusion plate 102, which is shown in FIG. 1 as being attached to a spinal column 104. The spinal column 104 includes a plurality of vertebrae 106, which may be cervical vertebrae.

Figure 2:
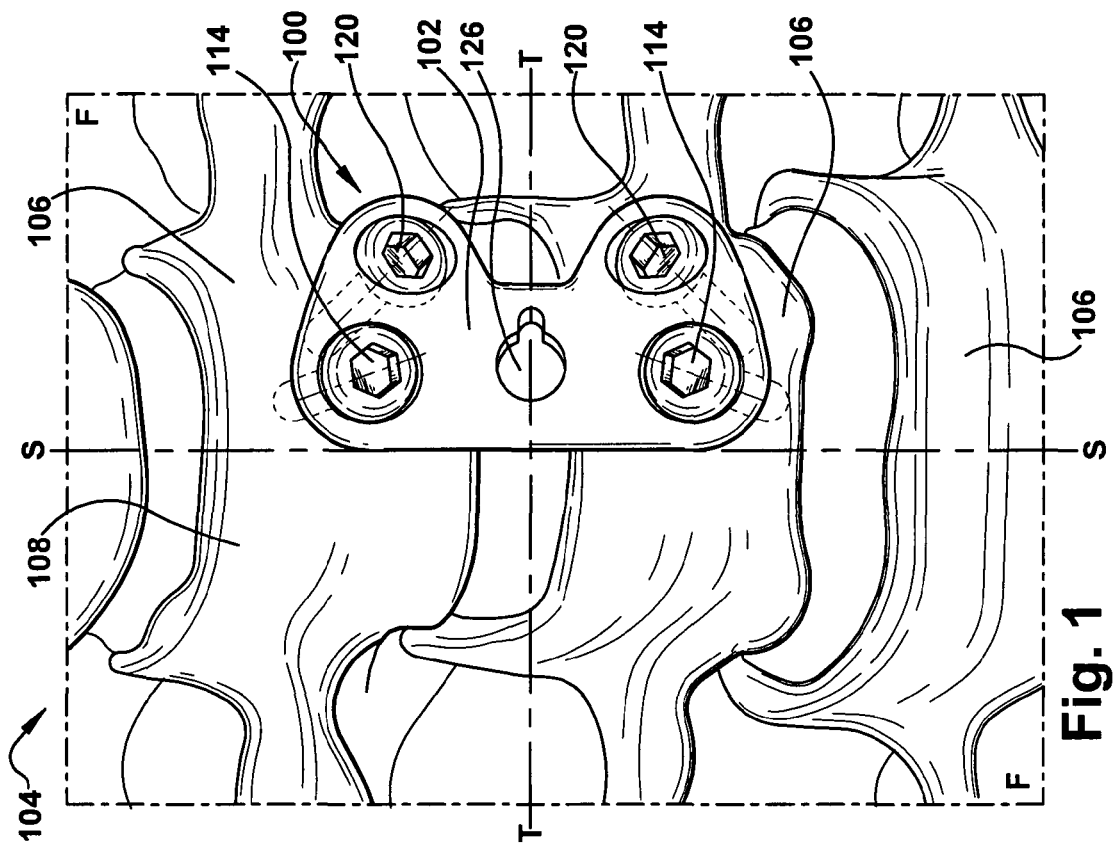
FIG. 2 is a frontal view of an exemplary embodiment of the present invention in a second mode.
Figure 3:
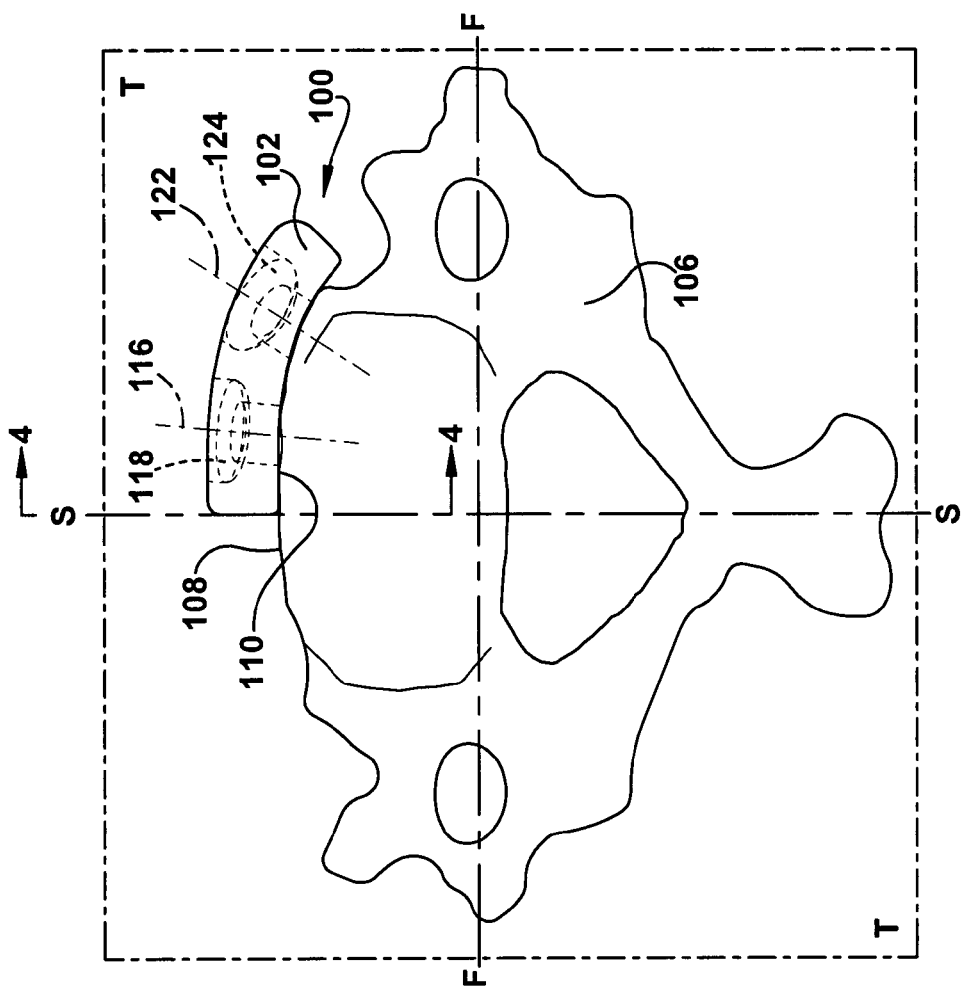
FIG. 3 is a cross-sectional transverse view of an exemplary embodiment of the present invention.

In FIGS. 1-4, a known three-dimensional orthogonal coordinate system comprising a frontal plane ("F-F"), a sagittal plane ("S-S"), and a transverse plane ("T-T") is illustrated in conjunction with the spinal column 104. Each of these three planes is perpendicular to the other two. While the frontal, sagittal, and transverse planes are depicted in the Figures as having certain positions in relation to the spinal column 104 for clarity of description, these planes may be defined in any desired relationship to the spinal column 104 as long as the planes maintain the orthogonal coordinate system as shown. For example, the transverse plane may pass through the body of a vertebra 106 instead of between vertebrae 106 as shown, or the frontal plane may bisect the spinal cord (not shown). However, such a changed relationship would only effect the description of, not the nature or substance of, the present invention. For clarity, the following description references a "midline sagittal plane" defined along a midline of the spinal column as depicted in FIGS. 1, 2, and 3.

The cervical fusion plate 102 may be positioned in an asymmetrical relationship with the midline sagittal plane. By "asymmetrical", what is meant herein is that at least a portion of the cervical fusion plate 102 located to one side of the midline sagittal plane has a different size or shape than the remaining portion of the cervical fusion plate 102 located to the opposite side of the midline sagittal plane. The cervical fusion plate 102 may be located wholly to one side of the midline sagittal plane. Optionally, the cervical fusion plate 102 itself has a symmetrical form but is positioned asymmetrically with respect to the midline sagittal plane to form the asymmetrical relationship with the midline sagittal plane. The cervical fusion plate 102 may also or instead be of substantially symmetrical form and/or placement with respect to a transverse plane.

The cervical fusion plate 102 is adapted to simultaneously engage a plurality of vertebrae 106 of the spinal column 104 to retain the engaged vertebrae 106 in a desired relationship, and the engaged vertebrae 106 need not be adjacent. For clarity, though, an engagement with two adjacent vertebrae 106 will be described herein.

Each vertebra 106 has an anterior surface 108 substantially centered about the midline sagittal plane. The cervical fusion plate 102 may engage a side portion of the anterior surface 108 to form the asymmetrical relationship with the midline sagittal plane.

The cervical fusion plate 102 may also include one or more optional features (not shown) which facilitate positioning of the cervical fusion plate 102 in relation to the spinal column 104 or engagement of the cervical fusion plate 102 with the vertebrae 106. For example, an inner plate side 110 of the cervical fusion plate 102, located adjacent the vertebrae 106, may include at least one location rib arranged transversely on the inner plate side 110 and adapted for at least partial insertion into an intervertebral space 112 defined between two adjacent vertebrae. At least a portion of the inner plate side 110 may be shaped to substantially follow a contour of at least a portion of the anterior surfaces 108 of the vertebrae 106. The cervical fusion plate 102 may include at least one placement spike or peg adapted for insertion into a vertebra 106 to temporarily hold the cervical fusion plate 102 and the vertebra 106 in a fixed orientation until a more permanent engagement can be made. Any or all of these options may be readily provided for a desired application of the cervical fusion apparatus 100 by one of ordinary skill in the art.

The cervical fusion plate 102 engages the vertebrae 106 with the aid of at least two primary fasteners 114. Each primary fastener 114 has a longitudinal axis 116 and is adapted for insertion through a primary fastener opening 118 of the cervical fusion plate 102. The cervical fusion plate 102 optionally also engages the vertebrae 106 with the aid of at least two secondary fasteners 120, as shown in the exemplary embodiment of FIGS. 1-4. Each secondary fastener 120 has a longitudinal axis 122 and is adapted for insertion through a secondary fastener opening 124 of the cervical fusion plate 102.

Each primary and secondary fastener 114 and 120 may be of any suitable type (e.g., bolt, screw, spike, barbed rod, adhesive/peg, or the like). The primary and secondary fasteners 114 and 120 of the cervical fusion apparatus 100 need not be matched in type, size, material, position, or any other characteristic and may be readily selected as desired by one of ordinary skill in the art.

The primary and secondary fastener openings 118 and 124 may have any suitable configuration, such as substantially round holes, elongated slots, or open-sided notches in the cervical fusion plate 102. The primary and secondary fastener openings 118 and 124 may be filleted, chamfered, countersunk, or otherwise shaped to accept the corresponding primary or secondary fastener 114 or 120, respectively, in a snug mating relationship and optionally prevent any portion of the primary or secondary fastener, such as a fastener head, from protruding from the cervical fusion plate 102 once implantation is complete. In addition, the primary and secondary fastener openings 118 and 124 may have associated therewith anchoring structures, such as retainer clips (not shown), to firmly anchor the primary and secondary fasteners 114 and 120, respectively, to at least one of the cervical fusion plate 102 and a vertebra 106.

There may be a plurality of primary and secondary fastener openings 118 and 124 provided at a variety of locations on the cervical fusion plate 102. In such case, the primary and secondary fasteners 114 and 120 would be inserted into chosen ones of the primary and secondary fastener openings 118 and 124, respectively, to position the primary and secondary fasteners as desired. Any remaining unused primary and secondary fastener openings 118 and 124 could be either left empty or plugged/filled.

A primary or secondary fastener opening 118 or 124 may be adapted to removably accept a surgical tool (not shown), to facilitate manipulation and steadying of the cervical fusion plate 102 during positioning of the cervical fusion plate 102 relative to the spinal column 104. Alternately, and as shown in the exemplary embodiment of FIGS. 1-2, a tool opening 126 could be provided in the cervical fusion plate 102 to perform such function.

Figure 4:
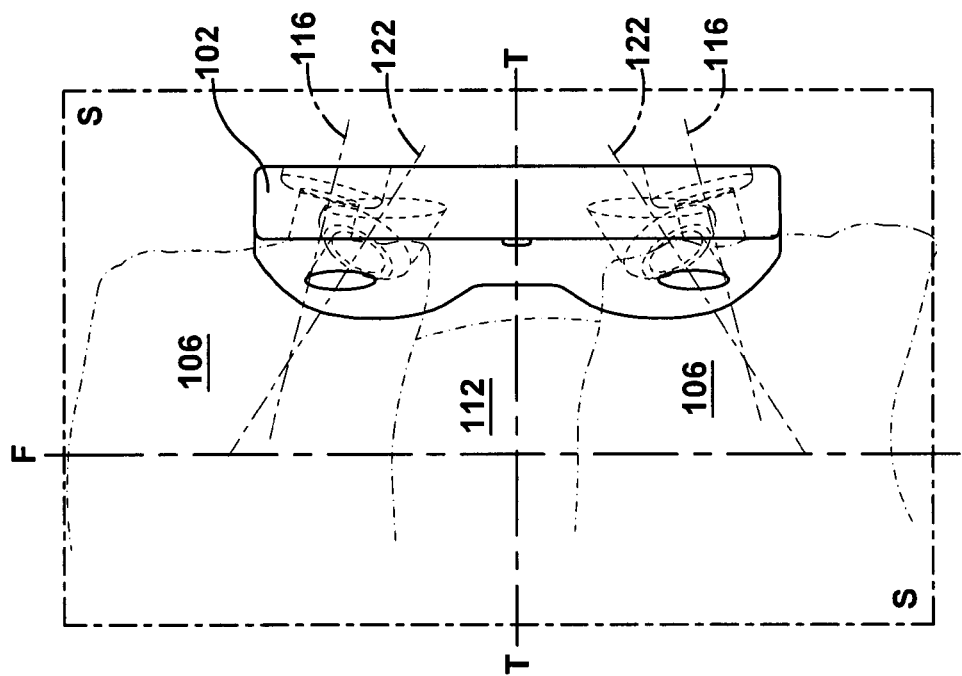
FIG. 4 is a cross-sectional sagittal view of an exemplary embodiment of the present invention.

The primary and secondary fastener openings 118 and 124 are optionally shaped to guide a chosen one of the primary or secondary fasteners 114 or 120, respectively, into a predetermined angular relationship with another chosen one of the primary or secondary fasteners 114 or 120, as in the exemplary embodiment of the present invention shown in FIGS. 2-4. The angular placements of the primary and secondary fasteners 114 and 120 with respect to the cervical fusion plate 102 and/or the vertebrae 106 may be determined by one of ordinary skill in the art, but should be chosen to engage the cervical fusion plate 102 and the vertebrae 106 together to retain the vertebrae in the desired spatial relationship while accommodating individual patient anatomy.

For example, and as shown in FIG. 4, the longitudinal axes 116 of the primary fasteners 114 in an exemplary embodiment of the present invention are each angled relative to the transverse plane when the primary fasteners 114 are inserted through the primary fastener openings 118. The primary fasteners 114 may also or instead be angled with respect to the midline sagittal plane, as shown in FIG. 3. The longitudinal axes 116 of two primary fasteners 114 may form a diverging angle as viewed from the midline sagittal plane as those primary fasteners 114 each extend into a vertebra 106, as shown in cross-section in FIG. 4. This diverging angle of the primary fasteners 114 may be in the range of 15-30 degrees, for example.

Likewise, and as shown in FIGS. 3-4, the longitudinal axes 122 of the secondary fasteners 120 in an exemplary embodiment of the present invention are each angled relative to the transverse plane when the secondary fasteners 120 are inserted through the secondary fastener openings 124. The secondary fasteners 120 may be angled with respect to both the transverse and midline sagittal planes, as shown in FIGS. 3-4. The longitudinal axes 122 of two secondary fasteners 120 may form a diverging angle as viewed from the midline sagittal plane as those secondary fasteners each extend into a vertebra 106, as shown in cross-section in FIG. 4. This diverging angle between the secondary fasteners 120 may be in the range of 0-80 degrees, for example.

Optionally, the longitudinal axes 116 and 122 of primary and secondary fasteners 114 and 120 form a converging angle in the transverse plane as the primary and secondary fasteners extend into a vertebra 106, as shown in cross-section in FIG. 3. This converging angle of the primary and secondary fasteners 114 and 120 may be in the range of 15-35 degrees, for example. This converging-angle arrangement may be repeated parallel to the transverse plane for each of a plurality of vertebrae 106 to be retained in a desired spatial relationship.

When the cervical fusion apparatus 100 is implanted in a patient, a surgeon dissects the patient's throat below the patient's chin to access the cervical spinal column 104 of the patient. Optionally, the throat dissection may be done asymmetrically with respect to the throat to minimize invasion of the throat while positioning the cervical fusion plate 102 in the desired relationship with the cervical spinal column 104. The surgeon then inserts the cervical fusion plate 102 into the throat dissection and maneuvers the cervical fusion plate 102 around the larynx and other throat structures to a position near the spinal column 104. The size or shape of the cervical fusion plate 104 may be chosen to minimize damage or irritation to the patient's throat during implantation while maintaining strength to retain the vertebrae 106 in the desired relationship after implantation. For example, the size of the cervical fusion plate 104 may be minimized in at least one dimension so that the surgeon can use the smallest possible incision to access the cervical spinal column 104, or so that the surgeon does not have to displace (and thereby traumatize) the larynx, trachea, and/or esophagus to the same extent as in the traditional midline placement in order to position the cervical fusion plate 104.

Once the cervical fusion plate 102 is located near the spinal column 104, the surgeon positions the cervical fusion plate 102 in an asymmetrical relationship with the midline sagittal plane of the cervical spinal column 104. A holder or other removable tool is optionally associated with a primary or secondary fastener opening 118 or 124, or a tool opening 126, to facilitate positioning and steadying of the cervical fusion plate 102 during implantation. The surgeon contacts a side portion of the anterior surface 108 of a first vertebra 106 and a side portion of the anterior surface 108 of a second vertebra 106 with the cervical fusion plate 102.

The surgeon optionally holds the cervical fusion plate 102 in engagement with the vertebrae 106 while drilling or tapping reception holes (not shown) in the vertebrae 106 to receive the primary and, when present, secondary fasteners 114 and 120. These reception holes should match the chosen primary and secondary fastener openings 118 and 124 for precise implantation of the cervical fusion apparatus 100. Alternately, the vertebrae 106 could be prepared with such reception holes before the cervical fusion plate 102 becomes engaged with the vertebrae 106. However, if the primary and, when present, secondary fasteners 114 and 120 are self-tapping, the surgeon need not prepare reception holes but instead might drill small pilot holes or even just initially penetrate the anterior surface 108 of the vertebrae 106 directly with the primary or secondary fasteners 114 or 120 to be installed.

Once the cervical fusion plate 102 has been positioned as desired and the vertebrae 106 have been prepared as needed to accept the primary and secondary fasteners 114 and 120, the surgeon inserts a first primary fastener 114 through a first primary fastener opening 118 and into the first vertebra 106. The surgeon also inserts a second primary fastener 114 through a second primary fastener opening 118 and into the second vertebra 106. Once these primary fasteners 114 have been tightened and anchored as desired, the cervical fusion apparatus 100 is operative to retain the engaged vertebrae 106 in the desired spatial relationship.

The surgeon may optionally implant secondary fasteners 120, following a substantially similar procedure, to further secure the desired spatial relationship of the vertebrae 106. When all of the desired primary and secondary fasteners 114 and 120 have been implanted to the surgeon's satisfaction, all tools are removed from the throat dissection and the patient's throat is closed in a known manner.

The method and apparatus of certain embodiments of the present invention, when compared with other apparatus and methods, may have the advantages of: being useful in a minimally invasive surgical procedure, allowing the patient's throat structures to remain largely in place during the operation, being usable in a timely and efficient manner, and being more economical to manufacture and use. Such advantages are particularly worthy of incorporating into the design, manufacture, and operation of a cervical fusion apparatus 100. In addition, the present invention may provide other advantages which have not yet been discovered.

While aspects of the present invention have been particularly shown and described with reference to the preferred embodiment above, it will be understood by those of ordinary skill in the art that various additional embodiments may be contemplated without departing from the spirit and scope of the present invention. For example, the elements of the present invention could be made of any variety or combinations of materials, though preferably all chosen materials are biocompatible; the primary and secondary fasteners 114 and 120 could be angled differently than described; the primary and secondary fasteners 114 and 120 could be inserted in a different order than described, the cervical fusion plate 102 could include various contours, apertures, or other shaping providing advantages in strength, weight, infection-resistance, cost, or the like; any desired number of vertebrae 106 could be engaged with the cervical fusion plate 102; or the engaged vertebrae 106 need not be adjacent. However, a device or method incorporating such an embodiment should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, the following is claimed:

1. A method of implanting a fusion plate to fuse two adjacent cervical vertebrae of the spinal column of a patient, the fusion plate having at least two primary fastener openings, the method comprising the steps of:
    dissecting a throat of the patient unilaterally with respect to a frontal midline of the spinal column of the patient;
    providing access through the throat dissection to the spinal column;
    inserting the fusion plate into the throat dissection to a position near the spinal column while minimizing displacement of a trachea, an esophagus, and other throat structures;
    positioning the fusion plate in an asymmetrical relationship with the frontal midline of the spinal column so that at least more than half of the fusion plate is located to one side of the frontal midline of the spinal column than the opposite side of the frontal midline of the spinal column;
    contacting a side portion, adjacent an anterior tubercle, of an anterior surface of a first cervical vertebra of the spinal column and a side portion, adjacent an anterior tubercle, of an anterior surface of a second cervical vertebra of the spinal column with the fusion plate;
    inserting a first primary fastener, having a longitudinal axis, through a first primary fastener opening of the fusion plate and into the first cervical vertebra such that the longitudinal axis of the first primary fastener is angled within a sagittal plane relative to a transverse plane of the spinal column; and
    inserting a second primary fastener, having a longitudinal axis, through a second primary fastener opening of the fusion plate and into the second cervical vertebra such that the longitudinal axis of the second primary fastener is angled within the sagittal plane relative to the transverse plane of the spinal column.

2. The method of claim 1, including the steps of:
    inserting a first secondary fastener through a first secondary fastener opening of the fusion plate and into the first cervical vertebra such that the longitudinal axis of the first secondary fastener is angled within the sagittal plane relative to the transverse plane; and
    inserting a second secondary fastener through a second secondary fastener opening of the fusion plate and into the second cervical vertebra such that the longitudinal axis of the second secondary fastener is angled within the sagittal plane relative to the transverse plane.

3. The method of claim 1, including the steps of:
    inserting the first secondary fastener through the first secondary fastener opening of the fusion plate and into the first cervical vertebra such that the longitudinal axis of the first secondary fastener is angled within both the sagittal and transverse planes; and
    inserting the second secondary fastener through the second secondary fastener opening of the fusion plate and into the second cervical vertebra such that the longitudinal axis of the second secondary fastener is angled within both the sagittal and transverse planes.

4. The method of claim 3, wherein the longitudinal axes of the first primary and first secondary fasteners form a converging angle of between 16 and 35 degrees, inclusive, in the transverse plane as the first primary and first secondary fasteners extend into the first cervical vertebra, and the longitudinal axes of the second primary and second secondary fasteners form a converging angle of between 16 and 35 degrees, inclusive, in the transverse plane as the second primary and second secondary fasteners extend into the second cervical vertebra.

5. The method of claim 1, including the step of contacting at least a portion of the anterior surfaces adjacent the anterior tubercles of the first and second cervical vertebrae with an inner plate side of the fusion plate, the inner plate side being curved within the transverse plane to substantially follow a contour of the anterior surfaces adjacent the anterior tubercles of the first and second cervical vertebrae.

6. The method of claim 1, wherein a footprint of the fusion plate is asymmetrical in at least two of the sagittal, transverse, and frontal planes.

7. The method of claim 1, wherein the fusion plate includes at least one indentation, at least a portion of the indentation intersecting a line linking centerlines of at least two of the first and second primary and secondary fastener openings.

8. The method of claim 1, wherein the cervical fusion plate may be located wholly to one side of the frontal midline of the spinal column.

* * * * *